(12) United States Patent
Skorheim et al.

(10) Patent No.: US 10,850,099 B2
(45) Date of Patent: Dec. 1, 2020

(54) TRANSCRANIAL STIMULATION SYSTEM AND METHOD TO IMPROVE COGNITIVE FUNCTION AFTER TRAUMATIC BRAIN INJURY

(71) Applicant: HRL Laboratories, LLC, Malibu, CA (US)

(72) Inventors: Steven W. Skorheim, Canoga Park, CA (US); Nicholas A. Ketz, Topanga, CA (US); Jaehoon Choe, Agoura Hills, CA (US); Praveen K. Pilly, West Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 253 days.

(21) Appl. No.: 15/983,629

(22) Filed: May 18, 2018

(65) Prior Publication Data

US 2018/0264264 A1 Sep. 20, 2018

Related U.S. Application Data (63) Continuation-in-part of application No. 15/332,787, filed on Oct. 24, 2016, now Pat. No. 10,307,592.

(60) Provisional application No. 62/245,730, filed on Oct. 23, 2015, provisional application No. 62/534,133, (Continued)

(51) Int. Cl.
| | |
|---|---|
| *A61N 1/36* | (2006.01) |
| *G16H 20/70* | (2018.01) |
| *A61M 21/00* | (2006.01) |
| *G16H 20/30* | (2018.01) |

(Continued)

(52) U.S. Cl.
CPC ......... *A61N 1/36025* (2013.01); *A61M 21/00* (2013.01); *A61N 1/025* (2013.01); *A61N 1/0484* (2013.01); *A61N 1/36034* (2017.08); *G16H 20/30* (2018.01); *G16H 20/70* (2018.01); *A61M 2021/0072* (2013.01); *A61M 2205/52* (2013.01); *A61M 2230/10* (2013.01)

(58) Field of Classification Search
CPC .... A61N 1/36025; A61N 1/20; A61B 5/0476; A61B 5/4836; A61B 5/4812
See application file for complete search history.

(56) References Cited

U.S. PATENT DOCUMENTS

| | | |
|---|---|---|
| 2011/0112590 A1 | 5/2011 | Wu et al. |
| 2011/0270345 A1 | 11/2011 | Johnston et al. |
| 2015/0112403 A1 | 4/2015 | Ruffini et al. |

(Continued)

FOREIGN PATENT DOCUMENTS

JP 2011-517962 A 6/2011

OTHER PUBLICATIONS

Notification of Transmittal of International Search Report and the Written Opinion of the International Searching Authority for PCT/US2018/033421; dated Jan. 22, 2019.

(Continued)

*Primary Examiner* — Rex R Holmes
(74) *Attorney, Agent, or Firm* — Tope-McKay & Associates (57) ABSTRACT

Described is a system for transcranial stimulation to improve cognitive function. During operation, the system generates a customized stimulation pattern based on damaged white matter. Further, data is obtained representing natural brain oscillations of a subject. Finally, while the subject is awake, (Continued)

one or more electrodes are activated in phase with the natural brain oscillations and based on the customized stimulation pattern.

23 Claims, 5 Drawing Sheets

Related U.S. Application Data filed on Jul. 18, 2017, provisional application No. 62/570,669, filed on Oct. 11, 2017.

(51) Int. Cl.
*A61N 1/02* (2006.01)
*A61N 1/04* (2006.01)

(56) References Cited

U.S. PATENT DOCUMENTS

2015/0119689 A1   4/2015   Pascual-Leone et al.
2018/0264264 A1   9/2018   Skorheim et al.

OTHER PUBLICATIONS

International Search Report of the International Searching Authority for PCT/US2018/033421; dated Jan. 22, 2019.
Written Opinion of the International Searching Authority for PCT/US2018/033421; dated Jan. 22, 2019.
Niogi, S. N., et al. "Extent of microstructural white matter injury in postconcussive syndrome correlates with impaired cognitive reaction time: a 3T diffusion tensor imaging study of mild traumatic brain injury." American Journal of Neuroradiology 29.5 (2008): pp. 967-973.
Kraus, Marilyn F., et al. "White matter integrity and cognition in chronic traumatic brain injury: a diffusion tensor imaging study." Brain 130.10 (2007): pp. 2508-2519.
Wolf, John A., and Paul F. Koch. "Disruption of network synchrony and cognitive dysfunction after traumatic brain injury." Frontiers in systems neuroscience 10 (2016), pp. 1-14.
Cote, Kimberly A., Catherine E. Milner, and Tamara A. Speth. "Altered sleep mechanisms following traumatic brain injury and relation to waking function." AIMS Neuroscience 2.4 (2015): pp. 203-228.
Lesniak, Marcin, et al. "Effects of repeated anodal tDCS coupled with cognitive training for patients with severe traumatic brain injury: a pilot randomized controlled trial." the Journal of head trauma rehabilitation 29.3 (2014): pp. E20-E29.
Reinhart, Robert MG, et al. "Synchronizing theta oscillations with direct-current stimulation strengthens adaptive control in the human brain." Proceedings of the National Academy of Sciences 112.30 (2015): pp. 9448-9453.
Roy, Abhrajeet, Bryan Baxter, and Bin He. "High-definition transcranial direct current stimulation induces both acute and persistent changes in broadband cortical synchronization: A simultaneous tDCS-EEG study." IEEE Transactions on Biomedical Engineering 61.7 (2014): pp. 1967-1978.
D.R. Rutgers, F. Toulgoat, J. Cazejust, P. Fillard, P. Lasjaunias and D. Ducreux. "White Matter Abnormalities in Mild Traumatic Brain Injury: A Diffusion Tensor Imaging Study," American Journal of Neuroradiology Mar. 2008, 29 (3) pp. 514-519.
Hui Xiao,Yang Yang, Ji-hui Xi, and Zi-qian Chen, M.D., "Structural and functional connectivity in traumatic brain injury," Neural Regen Res. Dec. 2015; 10(12): pp. 2062-2071.
Notification and International Preliminary Report on Patentability (Chapter I) for PCT/US2018/033421; dated Jan. 30, 2020.

TRANSCRANIAL STIMULATION SYSTEM AND METHOD TO IMPROVE COGNITIVE FUNCTION AFTER TRAUMATIC BRAIN INJURY

CROSS-REFERENCE TO RELATED APPLICATIONS

The present application is a Continuation-in-Part application of U.S. application Ser. No. 15/332,787, filed on Oct. 24, 2016, now issued as U.S. Pat. No. 10,307,592. U.S. application Ser. No. 15/332,787 is a non-provisional application of U.S. Provisional Application No. 62/245,730, filed on Oct. 23, 2015, the entirety of which are hereby incorporated herein by reference.

The present application is ALSO a non-provisional patent application of U.S. Provisional Application No. 62/534,133, filed on Jul. 18, 2017, the entirety of which is hereby incorporated by reference.

The present application is ALSO a non-provisional patent application of U.S. Provisional Application No. 62/570,669, filed on Oct. 11, 2017, the entirety of which is hereby incorporated by reference.

GOVERNMENT RIGHTS

This invention was made with government support under U.S. Government Contract Number W911NF-16-C-0018 and U.S. Government Contract Number N66001-16-c-4058. The government has certain rights in the invention.

BACKGROUND OF INVENTION

(1) Field of Invention

The present invention relates to brain stimulation system and, more specifically, to system for transcranial stimulation to improve cognitive function after traumatic brain injury.

(2) Description of Related Art

Traumatic brain injury (TBI) often results in brain damage that can have a severe and lasting impact on the quality of life of a subject. TBI somewhat selectively damages the long-range connections or the white matter of the brain (fiber tracts) (see the List of Incorporated Literature References, Reference Nos. 1 and 2), resulting in a disruption of synchronized activity across brain regions. White matter is the type of brain tissue containing the greatest concentration of far reaching axons, which carry information to distant parts of the brain. Brain areas communicate information most effectively when activity patterns in these areas synchronize. The extent to which this synchrony is disrupted by TBI is directly related to the degree of lost function (see Literature Reference No. 3). Thus, there is a desperate need to improve cognitive function after TBI.

Transcranial stimulation has been used to improve cognitive function in TBI patients in the past (see Literature Reference No. 5). However, the stimulation used was not subject or injury specific and did not focus on synchronizing cortical oscillations. As a result, non-targeted stimulations are unlikely to correct the disruption of long range communication believed to be the major factor in loss of function in mild to moderate TBI. Non-targeted tDCS has been used to globally increase synchrony but was not targeted to specific regions where synchrony was disrupted.

As noted above, previous work simply applied stimulation to the brain in nonspecific pattern and was not designed to enhance synchrony (see Literature Reference No. 5), or only focused of globally increasing synchrony in healthy individuals without regard to the particular type of synchrony loss in TBI patients (see Literature Reference Nos. 6 and 7). Such systems fail to remedy the long term effects of TBI.

Thus, a continuing need exists for a system that that applies stimulation to the brain in a specific pattern to enhance synchrony and cognitive function.

SUMMARY OF INVENTION

This disclosure is directed to a system for transcranial stimulation to improve cognitive function. In various embodiments, the system includes one or more processors and a memory, the memory being a non-transitory computer-readable medium having executable instructions encoded thereon, such that upon execution of the instructions, the one or more processors perform several operations, such as generating a customized stimulation pattern based on damaged white matter; obtaining data representing natural brain oscillations of a subject; and activating, while the subject is awake, one or more electrodes in phase with the natural brain oscillations and based on the customized stimulation pattern.

In yet another aspect, a skull cap having a plurality of electrodes is included.

In yet another aspect, the system further performs an operation of activating, while the subject is asleep and during a positive phase of slow-wave oscillations, one or more electrodes in the skull cap based on the customized stimulation pattern.

In another aspect, the customized stimulation pattern includes activating at least two electrodes in the skull cap to provide simultaneous pulses to regions on both sides of the damaged white matter.

In yet another aspect, the system further performs an operation of activating one or more electrodes in the skull cap based on STAMP patterns during task learning.

Additionally, activating the one or more electrodes includes creating patterns of stimulation in phase with neural activity to synchronize activity across damaged areas.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention is directed to a system for transcranial stimulation to improve cognitive function after traumatic brain injury. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) List of Incorporated Literature References

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Niogi, S. N., et al. "Extent of microstructural white matter injury in postconcussive syndrome correlates with impaired cognitive reaction time: a 3T diffusion tensor imaging study of mild traumatic brain injury." American Journal of Neuroradiology 29.5 (2008): 967-973.
2. Kraus, Marilyn F., et al. "White matter integrity and cognition in chronic traumatic brain injury: a diffusion tensor imaging study." Brain 130.10 (2007): 2508-2519.
3. Wolf, John A., and Paul F. Koch. "Disruption of network synchrony and cognitive dysfunction after traumatic brain injury." Frontiers in systems neuroscience 10 (2016).
4. Cote, Kimberly A., Catherine E. Milner, and Tamara A. Speth. "Altered sleep mechanisms following traumatic brain injury and relation to waking function." AIMS Neuroscience 2.4 (2015): 203-228.
5. Lesniak, Marcin, et al. "Effects of repeated anodal tDCS coupled with cognitive training for patients with severe traumatic brain injury: a pilot randomized controlled trial." *The Journal of head trauma rehabilitation* 29.3 (2014): E20-E29.
6. Reinhart, Robert M G, et al. "Synchronizing theta oscillations with direct-current stimulation strengthens adaptive control in the human brain." Proceedings of the National Academy of Sciences 112.30 (2015): 9448-9453.
7. Roy, Abhrajeet, Bryan Baxter, and Bin He. "High-definition transcranial direct current stimulation induces both acute and persistent changes in broadband cortical synchronization: A simultaneous tDCS-EEG study." IEEE Transactions on Biomedical Engineering 61.7 (2014): 1967-1978.
8. D. R. Rutgers, F. Toulgoat, J. Cazejust, P. Fillard, P. Lasjaunias and D. Ducreux. "White Matter Abnormalities in Mild Traumatic Brain Injury: A Diffusion Tensor Imaging Study," American Journal of Neuroradiology March 2008, 29 (3) 514-519;
9. Hui Xiao, Yang Yang, Ji-hui Xi, and Zi-qian Chen, M. D., "Structural and functional connectivity in traumatic brain injury," Neural Regen Res. 2015 December; 10(12): 2062-2071.

(2) Principal Aspects

Various embodiments of the invention include three "principal" aspects. The first is a system for system for transcranial stimulation. The system is typically in the form of a computer system operating software or in the form of a "hard-coded" instruction set and includes all the necessary components to perform the operations described herein, such as sensors, stimulation cap with electrodes, etc. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

Figure 1:
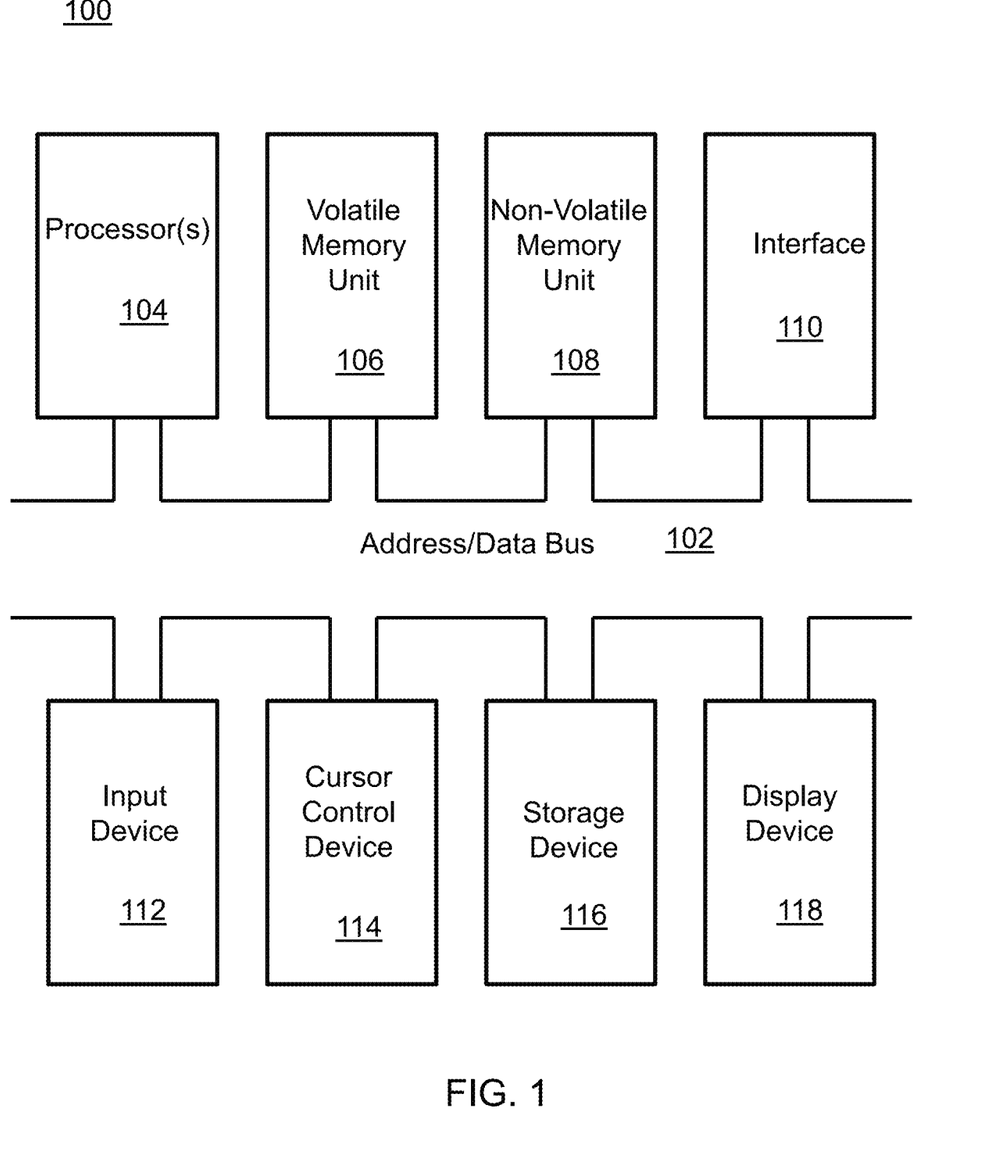
FIG. 1 is a block diagram depicting the components of a system according to various embodiments of the present invention.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
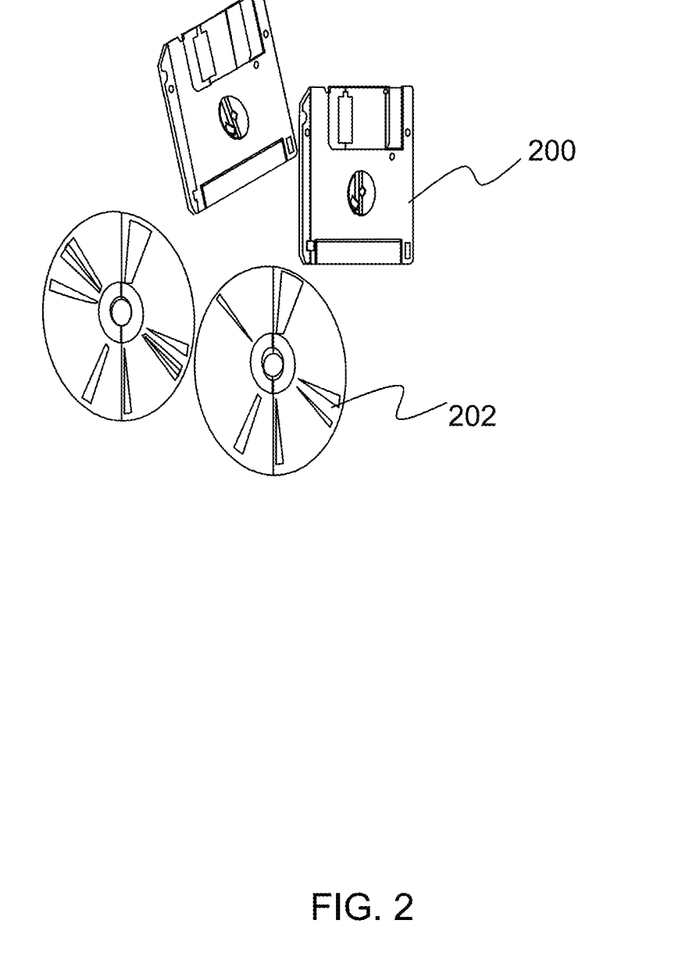
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Introduction

As noted above, traumatic brain injury (TBI) somewhat selectively damages the long-range connections or the white matter of the brain (fiber tracts), resulting in a disruption of synchronized activity across brain regions. Brain areas communicate information most effectively when activity patterns in these areas synchronize. The system of this disclosure applies a synchronizing stimulation that will enhance communication across areas of tissue damage, thus restoring some of the endogenous function lost subsequent to TBI. During slow-wave sleep (SWS), the whole cortex of the brain alternates together in active and inactive phases with a cycle of 0.5-1.2 Hz. This is referred to as slow-wave activity. These slow waves of activity are important for restful sleep and for memory consolidation. Damaged long-range connections result in less synchronized slow-wave activity across distant regions of the cortex. This results in reduced SWS quality and greater time spent in SWS, which results in increased fatigue and decline in cognitive function (see Literature Reference No. 4). By applying transcranial alternating current stimulation (tACS) on both sides of a formerly interconnected region with a pattern that is in phase with the global slow wave oscillation, the present system amplifies and synchronizes the slow wave activity across the brain. This will improve memory consolidation during sleep and improve recovery prognosis for TBI patients as well as reduce the required sleep time and fatigue. Similarly, during waking behavior, non-phase-locked transcranial direct current stimulation (tDCS) can be used in TBI patients to restore canonical connectivity patterns shown in healthy individuals. This can improve general cognitive behavior, and more specifically, memory recall, by improving inter-regional cortical synchrony. Over the long term, this waking stimulation can also promote plasticity in damaged connections, ultimately leading to a return to pre-injury neural and behavioral patterns.

Previous work simply applied stimulation to the brain in nonspecific pattern and was not designed to enhance synchrony (see Literature Reference No. 5), or only focused of globally increasing synchrony in healthy individuals without regard to the particular type of synchrony loss in TBI patients (see Literature Reference Nos. 6 and 7). The system described herein improves upon the prior art by also targeting regions specific to the individual's injury and brain structure, as identified through functional magnetic resonance imaging (fMRI), diffusor tensor imaging (DTI), and/or electrophysiological recordings obtained through electroencephalograms (EEG).

This disclosure provides a system and method to partially restore cognitive and memory function after TBI by applying synchronizing transcranial stimulation to multiple locations on the cortex. By using the appropriate pattern of electrode stimulation, it is possible to facilitate the synchronized activity that is disrupted in traumatic brain injury. This will be applied both to synchronize normal waking activity and also to synchronize slow wave activity during sleep.

The system described herein can be used for rehabilitation or with other interventions employing closed-loop high density electroencephalography (HD-EEG) sensing and focal-transcranial alternating current stimulation (tACS) stimulation. The system can also be incorporated into existing stimulation systems, such as those produced by Neuroelectrics, Soterix Medical, and/or EGI. Neurolectrics is located at 210 Broadway, Suite 201, Cambridge 02139, Massachusetts, USA. Soterix Medical is located at 237 W 35th St, New York, N.Y. 10001, while EGI (or Electrical Geodesics, Inc.) is located at 500 East 4th Ave., Suite 200, Eugene, Oreg. 97401.

(4) Specific Details of Various Embodiments

Figure 3:
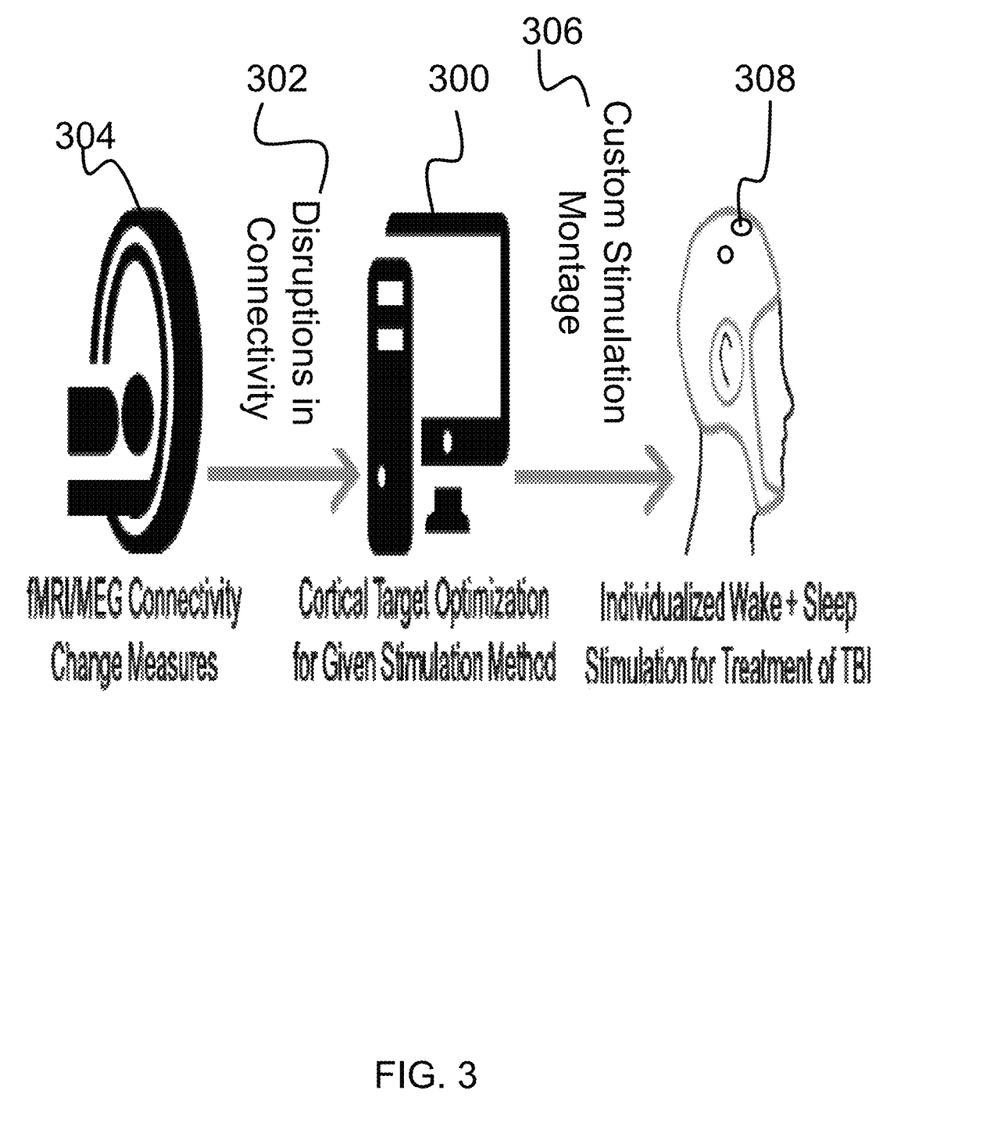
FIG. 3 is a flowchart illustrating a process for generating a customized stimulation montage for each traumatic brain injury (TBI) subject to restore synchronization.

This disclosure provides a system for customized transcranial stimulation to improve cognitive function after TBI. In general and as shown in FIG. 3, the system 300 identifies disruptions in connectivity 302 (i.e., damage to white matter) using data obtained from any suitable brain imaging or sensing technique 304 operable for sensing connectivity change measures (e.g., fMRI, magnetoencephalography (MEG), DTI, etc.). Based on the identified disruptions in connectivity 302 (damaged white matter), the system 300 generates a target optimization for a given stimulation method and corresponding custom stimulation montage 306. The system then activates electrodes 308 placed on the subject to implement the custom stimulation montage 306. The custom stimulation montage 306 results in individualized wake and sleep stimulation for treatment of TBI. Wake/Rest/Sleep patterns are targeted across multiple stimulation domains. Waking Stimulation is applied to increase recall and promote connectivity. Sleep Stimulation is applied to increase consolidation and sleep quality.

Figure 4:
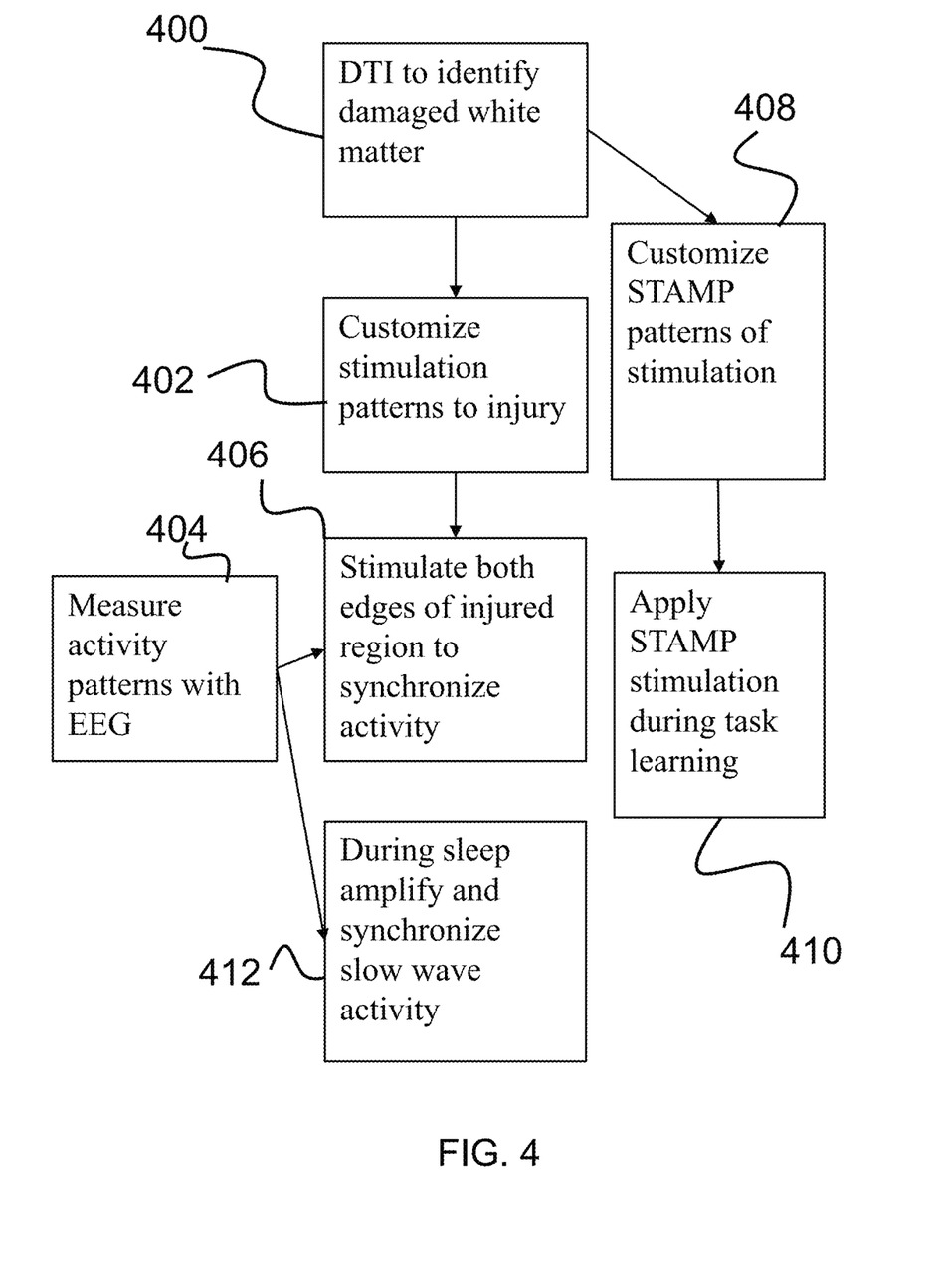
FIG. 4 is a flowchart illustrating a process for using transcranial stimulation (tCS) to increase synchrony and improve memory and cognition in TBI patients.

More specifically and as shown in FIG. 4, the system described herein identifies damaged white matter 400 and then implements the appropriate stimulation protocol. Diffusion tensor imaging and/or fMRI resting state connectivity are used to identify the damaged white matter 400 (i.e., locate areas where long range connections have been disrupted within a given individual). This is a relatively well-established method that is commonly known to those skilled in the art. As a non-limiting example, see Literature Reference Nos. 8 and 9.

Once the set of disrupted cortical connections is established (i.e., the damaged white matter is identified), a customized stimulation pattern 402 is established. The customized stimulation pattern 402 is based on identifying the specific regions of white matter where stimulation should be applied (and/or the electrodes being activated). For example, the customized stimulation pattern 402 is a pattern in which electrodes are placed proximate (e.g., on opposite sides) of the damaged white matter. While measuring activity patterns from an EEG 404, the system activates the electrodes to provide a stimulation 406 based on the customized stimulation pattern 402. More specifically and in various embodiments, in providing the stimulation 406, the system activates the electrodes to stimulate with simultaneous pulses on opposite sides of the regions of damaged white matter to enhance the synchrony of activity and oscillations. Stimulating in phase with natural brain oscillations (via the EEG 404 patterns) will increase the power and synchrony of oscillations. For example, while sensing the EEG 404 patterns, the system is able to monitor the natural brain oscillations. Based on that and as a non-limiting example, the system can increase the power and synchrony to the electrodes to cause the voltage provided by the electrodes to be in phase (match) with the natural brain oscillations.

This will restore disrupted paths of communication. In other words, the system activates the electrodes to stimulate the subject in phase with the EEG 404 measurements.

Further, during sleep, the system can be activated to apply stimulation 412 during the positive phase of slow wave oscillations. This both amplifies the slow wave events and synchronizes them across the damaged region resulting in more effective slow-wave-sleep (SWS). This builds from the SWS enhancement for healthy subjects disclosed previously in U.S. Provisional Application No. 62/570,669, the entirety of which is incorporated by reference as though fully set forth herein.

Current methods of designing electrode montages to target specific brain regions with electrical stimulation utilize a finite-elements model (FEM) of the brain generated from MRI imaging. This physical model allows simulated electrical currents to be applied to any spatial location of the scalp, and output which cortical areas will be subject to the majority of the electrical currents. While much more accurate than modelling the brain as a geometrically consistent object (such as a sphere), conventional FEM is still relatively inaccurate; the electrical properties of a limited number of tissues are taken into account, but the overall structure of the brain, including the complexity of fiber tracts and other interconnections between brain regions, are presently ignored. Diffusor Tensor Imaging (DTI) is a neuroimaging technique that identifies the orientation of white matter tracts with in the brain that carry signals across relatively distant regions of the brain through axonal fibers, thus allowing the system to trace the projections of neural aggregates across brain regions to a high degree of accuracy. This map of interconnects within the brain can be used to further increase the fidelity of the FEM and leverage its outputs to generate electrode montages (i.e., the customized stimulation pattern 402) that target electrical stimulation to the brain with greater precision and resolution.

Alternatively, the system can implement a customized "STAMP" pattern of stimulation 408. A "STAMP" pattern is a pattern of synchronized activity known to be associated with a given task, such as driving or speech production, can be used if a template is available from healthy populations. This template can include, but does not require, neural oscillation of specific patterns of connectivity to increase functional specificity. In order to further enhance learning, during training, specific patterns of stimulation may be applied 410. These "STAMP" patterns may later be reactivated to enhance consolidations of learned memories. The process of reactivating the "STAMP" patterns to enhance consolidation of learned memories is described in U.S. patent application Ser. No. 15/332,787, filed on Oct. 24, 2016, the entirety of which is incorporated by reference as though fully set forth herein. The "STAMP" can be optimized based on maximizing the orthogonality of electric fields, or current flows, in the individual injured heads in the voxels of the brain volume most relevant to a task of interest. Essentially, STAMPs are chosen to be maximally differentiable from each other; to have as much difference as possible in their effective stimulation.

(5) Control of a Device.

Figure 5:
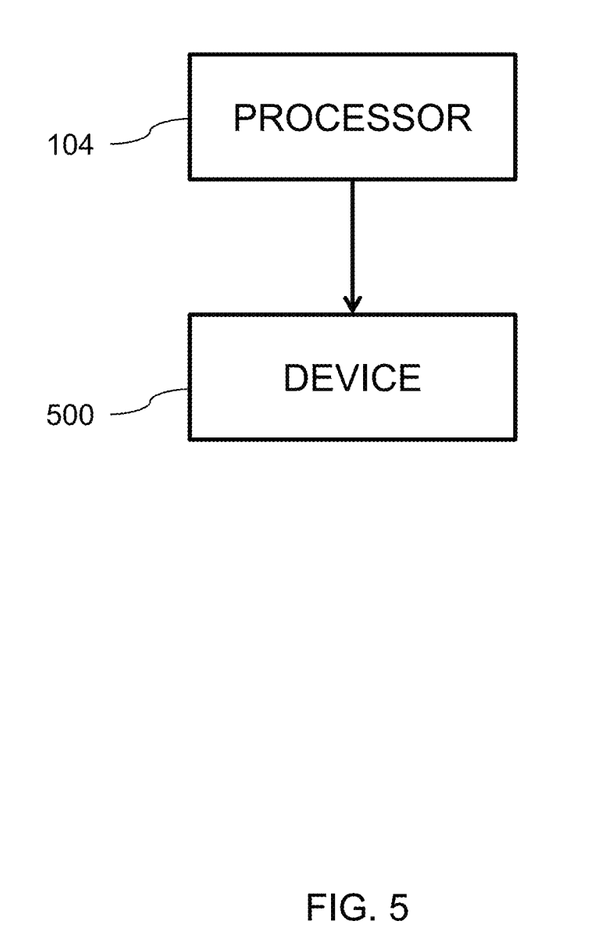
FIG. 5 is a block diagram depicting control of a device according to various embodiments.

As shown in FIG. 5, a processor 104 may be used to control a device 500 (e.g., electrodes) based on determined when to apply the tCS. The device 500 is any suitable device that can be used to provide a transcranial stimulation to a subject, non-limiting examples of which include a skull cap (such as shown in FIG. 3) with electrodes or an array of electrodes that is otherwise attachable with a subject's scalp. In essence, the processor 104 uses any device 500 (e.g., array of electrodes arranged on a skull cap or head cap) that can amplify and redistribute a measured electrical signal to synchronize electrical activity across the damaged brain regions.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

In summary, described is a targeted transcranial stimulation system that utilizes a custom stimulation pattern to enhance synchrony and improve function after TBI. The system is capable of improving both short-term task performance and long-term prognosis for traumatic brain injury patients. Targeted stimulation montages stimulate specific regions on either side of the damaged white matter. Synchronizing stimulation facilitates communication between brain regions, which facilitates learning, and helps to reestablish long-range functional connections. Further, stimulation during sleep can help to synchronize slow wave oscillations, restoring sleep quality and memory consolidation to near pre-injury levels. Additionally, recently acquired memories just prior to injury, which have not been adequately consolidated for long-term storage in neocortex, have a higher probability of being saved with TBI-aware closed-loop oscillatory stimulation to enhance memory consolidation during sleep. Remote, previously consolidated memories that have been rendered inaccessible as a result of TBI, can be recovered by functionally restoring long-range connectivity to improve signal-to-noise ratio of distributed pattern completion induced by memory cues. Deficits in forming new memories can be mitigated by restored functional connectivity from the hippocampus to more distant cortical regions, and among various task-relevant cortical regions, and also from improved memory consolidation during sleep with TBI-aware stimulation patterns. Finally, the processes described herein can be combined with the STAMP method, allowing the waking tagging and sleep consolidation of specific memories and skills using task-specific and TBI-specific STAMPs customized to the patient.

What is claimed is:

1. A system for transcranial stimulation to improve cognitive function, the system comprising:
one or more processors and a memory, the memory being a non-transitory computer-readable medium having executable instructions encoded thereon, such that upon execution of the instructions, the one or more processors perform operations of:
generating a customized stimulation pattern based on damaged white matter;
obtaining data representing natural brain oscillations of the subject; and
activating, while the subject is awake, one or more electrodes in phase with the natural brain oscillations and based on the customized stimulation pattern.

2. The system as set forth in claim 1, further comprising a skull cap having a plurality of electrodes, wherein the one or more electrodes are included in the plurality of electrodes.

3. The system as set forth in claim 2, further comprising an operation of activating, while the subject is asleep and during a positive phase of slow-wave oscillations, a second set of one or more of the plurality of electrodes in the skull cap based on the customized stimulation pattern.

4. The system as set forth in claim 3, wherein the customized stimulation pattern includes activating at least two of the plurality of electrodes in the skull cap to provide simultaneous pulses to regions on both sides of the damaged white matter.

5. The system as set forth in claim 4, further comprising an operation of activating a third set of one or more of the plurality of electrodes in the skull cap based on STAMP patterns during task learning.

6. The system as set forth in claim 5, wherein activating the one or more electrodes includes creating patterns of stimulation in phase with neural activity to synchronize activity across damaged white matter.

7. The system as set forth in claim 1, further comprising an operation of activating, while the subject is asleep and during a positive phase of slow-wave oscillations, a second set of one or more electrodes, based on the customized stimulation pattern.

8. The system as set forth in claim 1, wherein the one or more electrodes includes at least two electrodes, and wherein the customized stimulation pattern includes activating the at least two electrodes to provide simultaneous pulses to regions on both sides of the damaged white matter.

9. The system as set forth in claim 1, further comprising an operation of activating a second set of one or more electrodes based on STAMP patterns during task learning.

10. The system as set forth in claim 1, wherein activating the one or more electrodes includes creating patterns of stimulation in phase with neural activity to synchronize activity across damaged white matter.

11. A computer program product for transcranial stimulation to improve cognitive function, the computer program product comprising:
a non-transitory computer-readable medium having executable instructions encoded thereon, such that upon execution of the instructions by one or more processors, the one or more processors perform operations of:
generating a customized stimulation pattern based on damaged white matter;
obtaining data representing natural brain oscillations of the subject; and
activating, while the subject is awake, one or more electrodes in phase with the natural brain oscillations and based on the customized stimulation pattern.

12. The computer program product as set forth in claim 11, further comprising an operation of activating, while the subject is asleep and during a positive phase of slow-wave oscillations, a second set of one or more electrodes based on the customized stimulation pattern.

13. The computer program product as set forth in claim 12, wherein the one or more electrodes includes at least two electrodes, and wherein the customized stimulation pattern includes activating the at least two electrodes to provide simultaneous pulses to regions on both sides of the damaged white matter.

14. The computer program product as set forth in claim 13, further comprising an operation of activating a third set of one or more electrodes based on STAMP patterns during task learning.

15. The computer program product as set forth in claim 14, wherein activating the third set of one or more electrodes includes creating patterns of stimulation in phase with neural activity to synchronize activity across damaged white matter.

16. The computer program product as set forth in claim 11, wherein the one or more electrodes includes at least two electrodes, and wherein the customized stimulation pattern includes activating the at least two electrodes to provide simultaneous pulses to regions on both sides of the damaged white matter.

17. The computer program product as set forth in claim 11, further comprising an operation of activating a second set of one or more electrodes based on STAMP patterns during task learning.

18. The computer program product as set forth in claim 11, wherein activating the one or more electrodes includes creating patterns of stimulation in phase with neural activity to synchronize activity across damaged white matter.

19. A computer implemented method for transcranial stimulation to improve cognitive function, the method comprising an act of:
causing one or more processors to execute instructions encoded on a non-transitory computer-readable medium, such that upon execution, the one or more processors perform operations of:
generating a customized stimulation pattern based on damaged white matter;
obtaining data representing natural brain oscillations of the subject; and
activating, while the subject is awake, one or more electrodes in phase with the natural brain oscillations and based on the customized stimulation pattern.

20. The method as set forth in claim 19, further comprising an operation of activating, while the subject is asleep and during a positive phase of slow-wave oscillations, a second set of one or more electrodes based on the customized stimulation pattern.

21. The method as set forth in claim 19, wherein the one or more electrodes includes at least two electrodes, and wherein the customized stimulation pattern includes activating the at least two electrodes to provide simultaneous pulses to regions on both sides of the damaged white matter.

22. The method as set forth in claim 19, further comprising an operation of activating a second set of one or more electrodes based on STAMP patterns during task learning.

23. The method as set forth in claim 19, wherein activating the one or more electrodes includes creating patterns of stimulation in phase with neural activity to synchronize activity across damaged white matter.

* * * * *